United States Patent
Waysbeyn et al.

(10) Patent No.: US 10,857,341 B2
(45) Date of Patent: Dec. 8, 2020

(54) REVERSIBLY REMOVABLE SELF-ADJUSTING PORT

(71) Applicant: VIGOR MEDICAL TECHNOLOGIES, LTD, Nesher (IL)

(72) Inventors: Igor Waysbeyn, Haifa (IL); Irina Kavounovski, Haifa (IL)

(73) Assignee: VIGOR MEDICAL TECHNOLOGIES, LTD, Nesher (IL)

( * ) Notice: Subject to any disclaimer, the term of this patent is extended or adjusted under 35 U.S.C. 154(b) by 271 days.

(21) Appl. No.: 16/090,392

(22) PCT Filed: Mar. 31, 2017

(86) PCT No.: PCT/US2017/025310
§ 371 (c)(1),
(2) Date: Oct. 1, 2018

(87) PCT Pub. No.: WO2017/173231
PCT Pub. Date: Oct. 5, 2017

(65) Prior Publication Data
US 2019/0117949 A1 Apr. 25, 2019

Related U.S. Application Data (60) Provisional application No. 62/316,082, filed on Mar. 31, 2016.

(51) Int. Cl.
*A61B 1/32* (2006.01)
*A61M 39/02* (2006.01)
*A61B 17/34* (2006.01)
*A61M 1/04* (2006.01)
*A61B 17/00* (2006.01)

(52) U.S. Cl.
CPC ..... *A61M 39/0247* (2013.01); *A61B 17/3415* (2013.01); *A61B 17/3496* (2013.01); *A61M 1/04* (2013.01); *A61M 39/02* (2013.01); *A61B 2017/00367* (2013.01); *A61B 2017/00991* (2013.01); *A61B 2017/3484* (2013.01); *A61B 2017/3492* (2013.01); *A61M 2039/0273* (2013.01); *A61M 2039/0291* (2013.01); *A61M 2210/101* (2013.01)

(58) Field of Classification Search
CPC combination set(s) only.
See application file for complete search history.

(56) References Cited

U.S. PATENT DOCUMENTS 8,435,174 B2 * 5/2013 Cropper ............ A61B 17/3421
600/203

\* cited by examiner

*Primary Examiner* — Sameh R Boles
(74) *Attorney, Agent, or Firm* — Guy Levi; The IP Law Firm of Guy Levi, LLC (57) ABSTRACT

The present disclosure is directed to a reversibly removable self-adjusting, perforating and/or guiding port configured to automatically retract a perforating blade or guiding rod upon entering a body cavity, while providing a substantially hermetic seal across the body cavity's wall.

16 Claims, 6 Drawing Sheets

REVERSIBLY REMOVABLE SELF-ADJUSTING PORT

CROSS REFERENCE TO RELATED APPLICATIONS

This patent application is a U.S. National Phase filing of co-pending, commonly owned PCT Application No. PCT/US2017/025310, filed Mar. 31, 2017, which claims priority from U.S. Provisional Application No. 62/316,082, filed 31 Mar. 2016 both which are incorporated herein by reference in their entirety.

BACKGROUND

The present disclosure relates to a port. Specifically, the disclosure relates to a self-adjusting, perforating port configured to automatically retract a perforating blade upon entering a body cavity.

For example, traumatic pneumothorax can occur as the result of accident or injury, either iatrogenic due to medical procedures performed to the chest cavity, or following chest trauma and resultant disruption of pleural integrity (e.g., following gunshot wound, stabbing or shrapnel related injuries). Also, mechanical ventilation used to treat adults and neonates with respiratory distress, can often be performed at pressures greater than one atmosphere, occasionally leading to barotrauma from this increased pressure—results in lung disruption. Following chest trauma or lung barotrauma, air may enter the chest cavity via the damaged lung parenchyma, or through a defect in the chest wall, causing the lung to collapse.

Depending on the indication, in other words, pneumothorax, tension pneumothorax, hemothorax, large pleural effusion, empyema, chylothorax and the like, an incision is made in the chest. For example, for complex pneumothorax, the incision is made between the $4^{th}$ and $5^{th}$ intercostal space in the safety triangle, apically in certain cases and basally in others. Conversely, for spontaneous pneumothorax, incision is made in the $2^{nd}$ intercostal space on the chest, above the pectoral muscle. Moreover stabbing to the pleural area, or gunshot wounds (GSW) may vary and present points of entry that are diverse both in angle and in depth of tissue to be traversed in order to effectively drain the pleural cavity. Each location may present different risks for internal injury upon inserting a trocar, lance or stylet whereby penetration of the chest may damage pleura, lung, great vessels, heart, mediastinum, diaphragm and abdominal contents.

Accordingly, there is a need for a single device that can be safely and quickly used by less experienced medical personnel, including first responders, to quickly and easily treat patients suffering from pneumothorax, tension pneumothorax, hemothorax, large pleural effusion, empyema, chylothorax on battlefields, conditions of mass casualties, conditions of environmental chemical, biologic, or radiologic contamination, as well as in more conventional settings, such as within ambulances and hospitals and all while minimizing risks of injuring internal organs.

SUMMARY

In an embodiment, provided herein is a pressure sensitive, self-adjustable port, comprising: a handle member comprising pressure sensitive actuation means; a shunt bobbin operably coupled to the handle member, the shunt bobbin comprising: a flanged sleeve member having an elongated annular proximal end and a distal end having a flanged portion and a neck portion; and a telescopic concentric cannula having a flanged distal end and an elongated proximal end, operably slidably coupled to the distal flanged member, the concentric flanged cannula being distally biased; an expanding anchor operably coupled to the elongated proximal end of the telescopic concentric cannula and the elongated annular proximal end of the flanged member; and a perforating blade movable between operational expanded position and retracted stowed position, the perforating blade being operably coupled to the pressure sensitive actuation means, wherein the expanding anchor is biased towards the flanged portion and wherein once actuated, the perforating blade is configured to retract upon entering a body cavity.

In another embodiment, provided herein is a method of coupling a port to a subject's site across from a body cavity comprising: in a wound, or a predetermined site, positioning the proximal end of a pressure sensitive, self-adjustable surgical port, comprising a handle member comprising pressure sensitive actuation means; a shunt bobbin operably coupled to the handle member, the shunt bobbin comprising: a flanged sleeve member having an elongated annular proximal end and a distal end having a flanged portion and a neck portion; and a telescopic concentric cannula having a flanged distal end and an elongated proximal end, operably slidably coupled to the distal flanged member, the concentric flanged cannula being distally biased; an expanding anchor operably coupled to the elongated proximal end of the telescopic concentric cannula and the elongated proximal end of the flanged member; and a perforating blade movable between operational expanded position and stowed retracted position, the perforating blade being operably coupled to the pressure sensitive actuation means, wherein the flanged member is biased towards the anchor and wherein once actuated, the perforating blade is configured to retract upon entering a body cavity; actuating the pressure sensitive actuation means thereby extending the perforating end; by applying force on the distal end of the handle, perforating the site; and removing the handle member.

In yet another embodiment, provided herein is a kit comprising a pressure sensitive, self-adjustable port, comprising: a handle member comprising pressure sensitive actuation means; a shunt bobbin operably coupled to the handle member, the shunt bobbin comprising: a flanged sleeve member having an elongated annular proximal end and a distal end having a flanged portion and a neck portion; and a telescopic concentric cannula having a flanged distal end and an elongated proximal end, operably slidably coupled to the distal flanged member, the concentric flanged cannula being distally biased; an expanding anchor operably coupled to the elongated proximal end of the telescopic concentric cannula and the elongated annular proximal end of the flanged member; and a perforating blade movable between operational expanded position and retracted stowed position, the perforating blade being operably coupled to the pressure sensitive actuation means, wherein the expanding anchor is biased towards the flanged portion and wherein once actuated, the perforating blade is configured to retract upon entering a body cavity; a catheter; optionally an analgesic; and optionally a disinfectant.

In another embodiment, provided herein is a diaphragm closure comprising a first annular member, having an internal surface, an external surface, a distal end and a proximal end, the distal end of the external surface defining a radial channel, wherein the internal surface is adapted to operably couple to a predetermined liquid vessel; a second annular member having an internal surface, an external surface, a distal end and a proximal end, the distal end of the internal surface defining a radial channel, wherein the internal surface is operably coupled to the external surface of the first annular member; a flexible closure sleeve having a distal and a proximal annular mounting flanges at opposite ends thereof, with a median mounting flange disposed therebetween, the distal and proximal mounting flanges being engaged respectively in the distally disposed radial channel in the internal surface of the second annular member, and the median mounting flange operably coupled to the radial recess in the external surface of the first annular member, so as to be angularly moveable relative to the first annular member.

BRIEF DESCRIPTION OF THE DRAWINGS

The features of the reversibly removable perforating surgical port described herein will become apparent from the following detailed description when read in conjunction with the figures, which are exemplary, not limiting, and in which.

While the disclosure of the reversibly removable perforating surgical port described herein, is amenable to various modifications and alternative forms, specifics thereof have been shown by way of example in the drawings and will be further described in detail hereinbelow. It should be understood, however, that the intention is not to limit the disclosure to the particular embodiments described. On the contrary, the intention is to cover all modifications, equivalents, and alternatives.

DETAILED DESCRIPTION

Provided herein are embodiments of a device, methods and kits of a self-adjusting, perforating or guided port configured to automatically retract a perforating blade or guide wire upon entering a body cavity.

The port is reversibly and selectably installed, or in other words, can be removed post insertion in a body cavity without causing damage to the body or necessitating additional incisions. In other words, removing the port provided herein will not increase the size of the aperture created in the body wall. Moreover, the port can be reinserted after further sterilization.

Definitions

The term "coupled", including its various forms such as "operably coupling", "coupling" or "couplable", refers to and comprises any direct or indirect, structural coupling, connection or attachment, or adaptation or capability for such a direct or indirect structural or operational coupling, connection or attachment, including integrally formed components and components which are coupled via or through another component or by the forming process. Indirect coupling may involve coupling through an intermediary member or adhesive, or abutting and otherwise resting against, whether frictionally or by separate means without any physical connection.

In addition, for the purposes of the present disclosure, directional or positional terms such as "top", "bottom", "upper," "lower," "side," "front," "frontal," "forward," "rear," "rearward," "back," "trailing," "above," "below," "left," "right," "radial," "vertical," "upward," "downward," "outer," "inner," "exterior," "interior," "intermediate," etc., are merely used for convenience in describing the various embodiments of the present disclosure.

Likewise, the term "engage" and various forms thereof, when used with reference to an engaging element, for example in the engagement of protrusions 136A, 136B, refers in an embodiment to the application of any forces that tend to hold protrusions 136A, and 136B, and radial recess 115 together against inadvertent or undesired separating forces (e.g., such as may be introduced during insertion of the port). It is to be understood, however, that engagement does not in all cases require an interlocking connection that is maintained against every conceivable type or magnitude of separating force. Further, the term "engaging element" refers in another embodiment to one or a plurality of coupled components, at least one of which is configured for releasably engaging another element. Thus, this term encompasses both single part engaging elements and multi-part-assemblies, for example the handle member as a whole.

The terms "first," "second," and the like, herein do not denote any order, quantity, or importance, but rather are used to denote one element from another. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., pawl member(s) 133A, 133B includes one or more member). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

A more complete understanding of the self-adjusting perforating or guided ports described herein, their methods of use and kits comprising these ports, can be obtained by reference to the accompanying drawings. These figures (also referred to herein as "FIG.") are merely schematic representations based on convenience and the ease of demonstrating the present disclosure, and are, therefore, not intended to indicate relative size, scale and dimensions of the devices or components thereof, their relative size relationship and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Likewise, cross sections and various views are referred to on normal orthogonal coordinate system having XYZ axis, such that Y axis refers to front-to-back, X axis refers to side-to-side, and Z axis refers to up-and-down.

Figure 1:
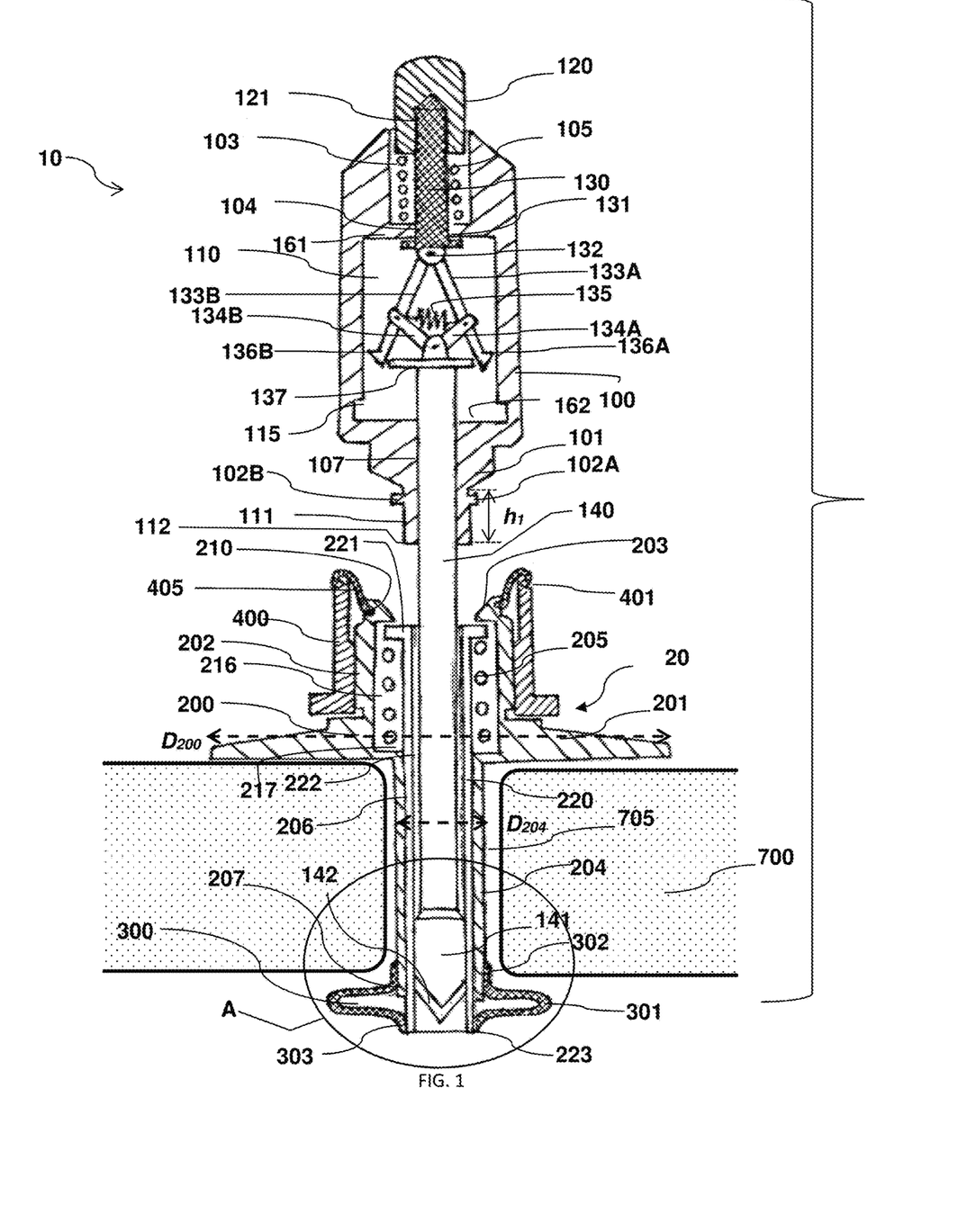
FIG. 1 illustrates a Y-Z cross section elevation view of an embodiment of the self-adjusting perforating port.

Turning now to FIG. 1, illustrating an embodiment pressure sensitive, self-adjustable port 10, comprising: handle member 100 comprising pressure sensitive actuation means. The pressure-sensitive actuation means comprise actuation rod 130 having a distal end configured to at least partially engage actuation knob 120, and a distal end hingedly coupled to a hinged quadrilateral pawl. In an embodiment, the term "pawl" or "pawl component" refers to a movable component which operates as a lever and which includes protuberances (or protrusions 136A, 136B), which engage a radial recess 115. In another embodiment, the term "pawl" refers to any hinged, pivoted, or adjustable structure adapted to temporarily and/or selectively engage an interfering structure, such as radial recess 115.

The hinged quadrilateral pawl comprising; first distal pawl member 133A and second distal pawl member 133B, each first 133A and second 133B distal pawl member having distal end 139A, 139B (not shown, see e.g., FIG. 2A, 2B), and proximal end with protrusion or perturbation(s) 136A, 136B, each which is configured to engage radial recess 115 defined in proximal end 162 of chamber 110 defined in distal head portion 101 of handle member 100, and distal end 139A, 139B hingedly coupled to actuation rod 130. The quadrilateral pawl can generally be an isosceles trapezoid, with overhanging sides. The quadrilateral pawl can further comprise first proximal pawl member 134A and second proximal pawl member 134B, with first proximal pawl member 134A having distal end 143A (not shown, see e.g., FIG. 2A, 2B), hingedly coupled to first distal pawl member 133A between distal end 139A and proximal end 136A of first distal pawl member 133A, and proximal end 144A hingedly coupled to perforating/guiding rod 140, and second proximal pawl member 134B having distal end 139B hingedly coupled to second distal pawl member 133B between distal end 139B and proximal end 136B of second distal pawl member 133B. The quadrilateral pawl further comprises pawl biaser 135 configured to bias distal end 143A of first proximal pawl member 134A to distal end 143B of second proximal pawl member 134B. Also illustrated in FIG. 1, is stopper 137, disposed below proximal end 144A, 144B of first and second proximal pawl members 134A, 134B and above proximal end 162 of internal chamber 110 defined in head portion 101 of handle member 100, configured to prevent proximal end 144A, 144B (not shown, see e.g., FIG. 2A, 2B), of first and second proximal pawl members 134A, 134B from entering bore 107 defined in proximal end 162 of internal chamber 110 defined in head portion 101 of handle member 100.

The pressure-sensitive actuation means also comprises actuation biaser 105 operably coupled to actuation knob 120 having and actuation rod 130. Actuation biaser 105 can be configured to distally bias actuation rod 130 into actuation knob's 120 well 121, and actuation knob 120 distally from handle member 100 distal end. Moreover, pressure-sensitive actuation means also comprises perforating rod 140, wherein perforating rod 140 can be configured to extend beyond proximal end 223 of telescopic concentric cannula 220. As illustrated in FIG. 1, distal end 101 of handle member 100 defines cylindrical chamber 103 with an aperture 104 connecting cylindrical chamber 103 with internal chamber 110. Further, actuation rod 130 can have a flanged proximal end 131 terminating in coupling 132, hingedly coupled to distal end(s) 139A, 139B (not shown, see e.g., FIG. 2A, 2B), of distal pawl member(s) 133A, 133B. Flanged proximal end 131 can be configured to abut proximal end 162 of chamber 110. A skilled artisan would recognize, that the location of actuation knob 120 does not need to be axially concentric with handle member 100, but can be radially disposed with proper mechanisms for transferring radial motion to axial motion to actuate the quadrilateral pawl. Likewise, the shape of handle member can be varied.

The pressure-sensitive actuation means also comprises shunt bobbin 20. Shunt bobbin 20 can be an assembly comprised of various components that is selectably removable post insertion to a body cavity. The term "selectably removable" means that shunt bobbin 20 can be removed upon demand by a user of the port. The shunt can be a lined bore allowing movement of fluid from the body cavity to the outside under controlled environment. The shunt bobbin head can be flanged sleeve member 200 having elongated annular midportion 204 and a distal end having flanged portion 201 and neck portion 202. The shunt bobbin assembly can further have telescopic concentric cannula 220 having flanged distal end 221 and elongated proximal end 222, operably slidably coupled to distal flanged member 201. Concentric flanged cannula 220 being distally biased. Concentric cannula 220 has open proximal end 223. As shown in FIG. 1, Sleeve member 200 having elongated annular midportion 204 accommodates telescopic concentric cannula 220 having flanged distal end 221 and elongated proximal end 222, operably slidably coupled to distal flanged member 201. As used herein, the term "accommodate" means that telescopic concentric cannula 220 having flanged distal end 221 and elongated proximal end 222, operably slidably coupled to distal flanged member 201 is configured at one or both ends to pass by sleeve member 200 having elongated annular midportion 204 and abut against the internal sidewall of elongated annular proximal end 204. In an embodiment, the term "slidably coupled" is used in its broadest sense to refer to elements which are coupled in a way that permits one element to slide or translate with respect to another element.

Shunt bobbin 20 is comprised of distal end having flanged portion 201 and neck portion 202 as a distal portion of shunt bobbin 20 (outside the body), elongated annular midportion 204 as the stem of shunt bobbin 20 (spanning the body cavity wall in bore 705), terminating with expanding anchor sleeve 300 as the proximal portion of the shunt bobbin 20. Flanged portion 201 can have a diameter that is at least three times (3x) larger than the outer diameter of sleeve member 200 having elongated annular proximal end 204. The outer diameter of elongated annular midportion 204 can depend on the indication for which the port is employed and can be between about 4 mm (about 12 French (Fr)) and about 15 mm (>40 Fr). For example, for tension pneumothorax the internal diameter of concentric cannula 220 can be between about 10 mm and about 12 mm, to accommodate a drainage tube of 28 Fr. Likewise, for neonatal large pleural fluid collections (e.g., empyema, chylothorax), the internal diameter of concentric cannula 220 can be between about 3 mm and about 6 mm, to accommodate a drainage tube of 8-12 Fr. Accordingly, Flanged portion 201 can have a diameter of between about 12 mm and about 50 mm.

The proximal end of shunt bobbin 20 can comprise expanding anchor sleeve 300 operably coupled to elongated proximal end 222 of telescopic concentric cannula 220 and elongated annular midportion 204 of the flanged member 200. As illustrated in FIG. 1, expanding anchor sleeve 300 is biased via adjusting biaser (e.g., a coil spring) 205 towards the flanged portion 201. As illustrated, flanged distal end 201 of the flanged sleeve member 200 defines a distally open cylindrical bore 216 with a diameter configured to accommodate flanged distal end 221 of the telescopic concentric cannula 220, and floor 217 defining a concentric proximal aperture 206 having a diameter configured to accommodate elongated proximal end 222 of telescopic concentric cannula 220. As illustrated, adjusting biaser 205, can be disposed in distally open cylindrical bore 216 defined in flanged distal end 201 of the flanged sleeve member 200 between flanged distal end 221 of telescopic concentric cannula 220 and floor 217 of distally open cylindrical bore 216.

In an embodiment, neck portion 202 of the distal end of the flanged sleeve member defines an external annular surface and an internal annular surface having lip 203 and is configured to releasably engage detent(s) 102A, 102B disposed on the outer surface of proximal portion 111 of the handle member 100, having proximal end 112. When inserted into distally open cylindrical bore 216, proximal portion's 111 proximal end 112 abuts flanged distal end 221 of telescopic concentric cannula 220, extending elongated proximal end 222 of telescopic concentric cannula 220 proximally beyond elongated annular midportion 204 of sleeve member 200, thereby extending expandable anchor 300 against adjusting biaser 205 and forming a tube with a substantially uniform outer diameter, the tube being comprised of elongated annular midportion 204 of sleeve member 200, expandable anchor sleeve 300 and elongated proximal end 222 of telescopic concentric cannula 220. Lip 203 in the internal annular surface of neck portion 202 can then engage detent(s) 102A, 102B, maintaining expandable anchor sleeve 300 stretched. Once detent(s) 102A, 102B disposed on the outer surface of proximal portion 111 of the handle member 100, having proximal end 112 are disengaged, biaser 205 will bias flanged distal end 221 of telescopic concentric cannula 220 distally, causing elongated proximal end 222 of telescopic concentric cannula 220 to slidably translate distally, causing expandable anchor sleeve 300 to expand and engage bore 705 in the body cavity wall and adjust the distance between expanded anchor sleeve 300 and the bottom surface of flanged distal end 201 of the flanged sleeve member 200.

As with the diameter of the bottom surface of flanged distal end 201 of the flanged sleeve member 200, so will the distance between expanded anchor sleeve 300 and the bottom surface of flanged distal end 201 of the flanged sleeve member 200 can be indication specific and adapted to be between about 1.5 cm and about 10 cm. For example, inserting a port after gut GSW may be longer than a port inserted to drain complex pneumothorax. In another embodiment, the kits provided herein comprising the ports described, may comprise a variety of ports of varying lengths and varying diameters e.g., of flanged sleeve member's 200 flanged portion 201, and internal diameter of elongated proximal end 222 of telescopic concentric cannula 220.

As indicated, to remove the port once inserted to the body cavity, proximal portion's 111 proximal end 112 of handle member 100 can be inserted into distally open cylindrical bore 216, abutting flanged distal end 221 of telescopic concentric cannula 220, thereby extending elongated proximal end 222 of telescopic concentric cannula 220 proximally beyond elongated annular midportion 204 of sleeve member 200—extending expandable anchor 300 against adjusting biaser 205 and forming a tube with a substantially uniform outer diameter and eliminating the proximal portion of shunt bobbin 20 which can then be removed through bore 705. Similarly, any rod, tube or member (e.g., a finger), rigid enough to overcome the force exerted by biaser 205 can be pressed against flanged distal end 221 of telescopic concentric cannula 220 and achieve the same result.

Perforating blade 141 used in the devices methods and kits described herein can be movable between operational expanded position and retracted stowed position, and wherein once actuated the perforating blade being operably coupled to the pressure sensitive actuation means, wherein the, perforating blade is configured to retract upon entering a body cavity. In addition, perforating blade 141 can be selectably detachable from perforating/guiding rod 140, such that for example, when inserting the port into a GSW, the blade can be detached and rod 140 becomes a guiding rod providing rigidity to elongated proximal end 222 of telescopic concentric cannula 220. As used herein, the term "selectably detachable" means that blade 141 can be detached from perforating/guiding rod 140 upon demand by a user without materially affecting the function of port 10.

Port 10 used in the methods and kits described herein, can further comprise a diaphragm valve assembly operably coupled to the external surface of neck portion 202 of shunt bobbin's 20 sleeve member 200, the diaphragm valve configured to rotate (or be angularly movable) between an open position and a closed position and be adapted to engage a tube (not shown, see e.g., FIG. 5, for example a catheter, or drainage tube) while sealing port 10 around the engaged tube.

As illustrated in FIG. 1, the diaphragm valve assembly can comprise an annular body member 400 being angularly movable relative to the neck portion 202 of shunt bobbin's 20 sleeve member 200 with annular body 400 having an external surface with distally disposed radial recess 401 and flexible closure sleeve 405 having a distal 406 and a proximal 407 annular mounting flanges (not shown) at opposite ends thereof, with a median mounting flange 408 (not shown disposed therebetween, the distal 406 and proximal 407 mounting flanges being engaged respectively in distally disposed radial recess 401 in the external surface of annular body member 400, and median mounting flange 408 (not shown) operably coupled to radial recess 210 in the external surface of neck portion 202 of shunt bobbin's 20 sleeve member 200, so as for annular body 400 to be angularly moveable relative to shunt bobbin's 20 sleeve member 200. Flexible closure sleeve 405 can be made from any resilient material that is biocompatible, for example, silicone, latex, nitinol, polyurethane, polyethylene, polytetrafluoroethylene-coated latex or an equivalently biocompatible material.

Accordingly and in an embodiment, provided herein is a pressure sensitive, self-adjustable port, comprising: a handle member comprising pressure sensitive actuation means; a shunt bobbin operably coupled to the handle member, the shunt bobbin comprising: a flanged sleeve member having an elongated annular proximal end and a distal end having a flanged portion and a neck portion; and a telescopic concentric cannula having a flanged distal end and an elongated proximal end, operably slidably coupled to the distal flanged member, the concentric flanged cannula being distally biased; an expanding anchor operably coupled to the elongated proximal end of the telescopic concentric cannula and the elongated annular proximal end of the flanged member; and a perforating blade movable between operational expanded position and retracted stowed position, the perforating blade being operably coupled to the pressure sensitive actuation means, wherein the expanding anchor is biased towards the flanged portion and wherein once actuated, the perforating blade is configured to retract upon entering a body cavity.

In another embodiment, the pressure sensitive self-adjusting ports described herein are used in the methods provided herein.

Figure 2A:
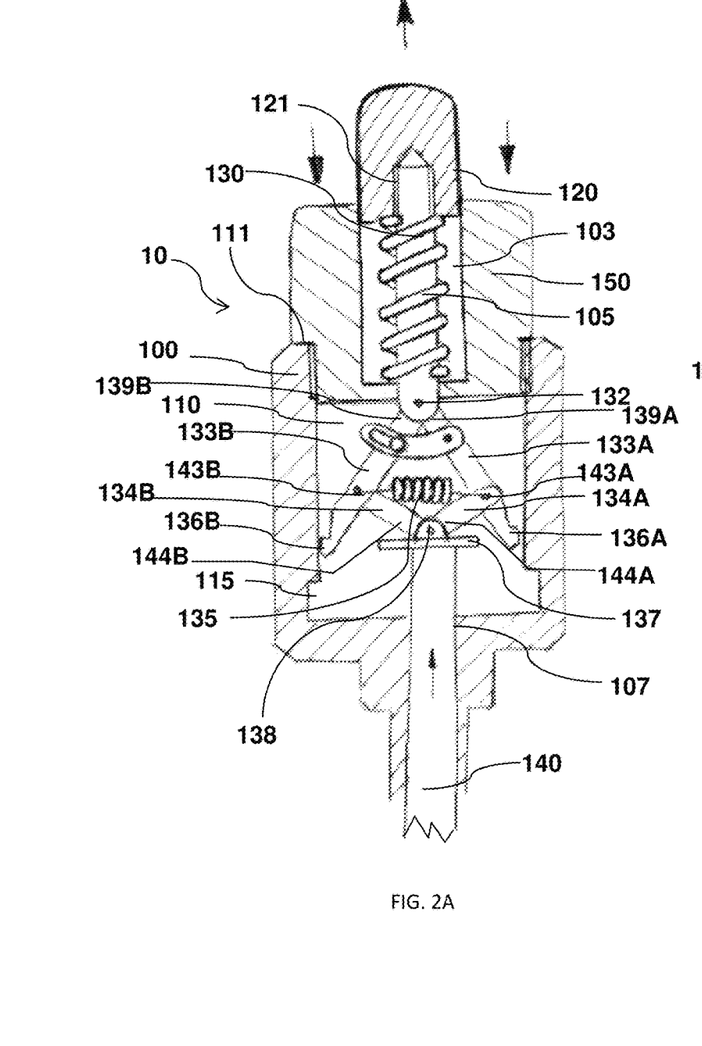
FIG. 2A illustrates a Y-Z cross section of the non-actuated distal end of the handle member, with FIG. 2B, illustrating a Y-Z cross section of the actuated distal end of the handle member.
Figure 2B:
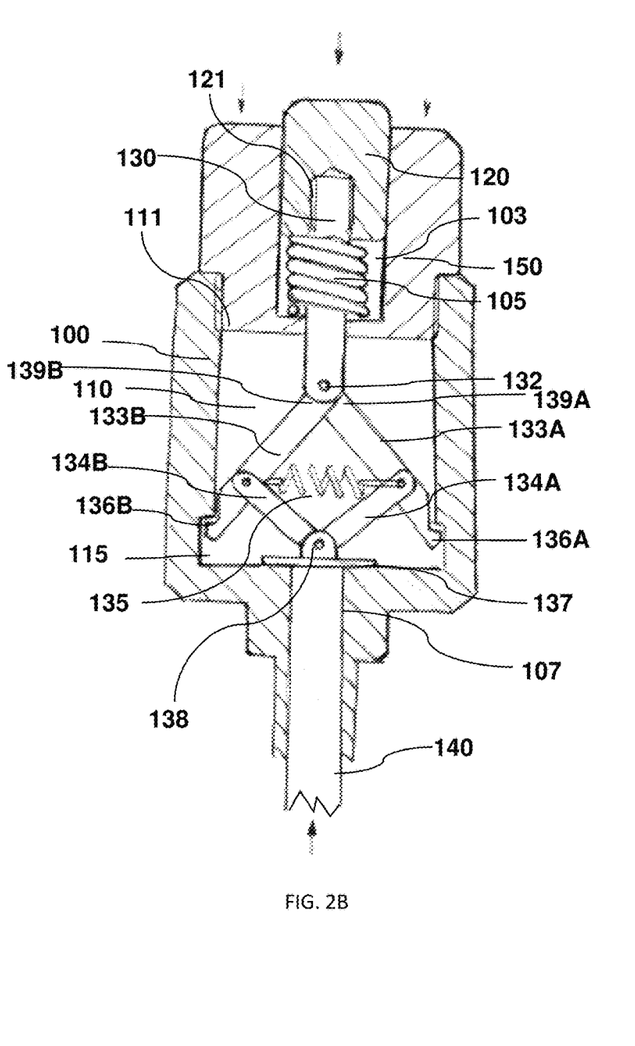

Turning now to FIGS. 1, 2A, and 2B, provided herein is a method of coupling port 10 described herein to a subject's site 700 across from a body cavity comprising: in a wound (e.g., 705), or a predetermined site 700, positioning proximal end 223 of telescopic concentric cannula 220 forming the proximal end of pressure sensitive, self-adjustable surgical port 10 actuating the pressure sensitive actuation means by pressing actuation knob 120, causing stopper 137 to abut proximal end 162 of chamber 110 thereby extending the perforating end 142 of perforating blade 141, as well as creating a fulcrum (in other words, the point on which the quadrilateral pawl rests or is supported and on which it pivots), causing quadrilateral pawl's distal members 133A, 133B to move proximally while expanding distal members 133A, 133B proximal end with protrusions 136A, 136B to the point where protrusions 136A, 136B are engaged within radial recess 115, and are forced against recess 115 upper edge by the pressure exerted distally while perforating or penetrating the insertion site 700 through insertion bore 705. The pressure on actuation knob 120 is removed when proximal end defining protrusions 136A, 136B is engaged within recess 115.

Applying force on distal end 101 of handle member 100 without applying pressure on actuation knob 120, perforating the site. Upon entering the body cavity, the pressure engaging distal end defining protrusions 136A, 136B is released, pawl biaser 135 biases distal ends 143A and 143B towards each other, causing actuation biaser 105 to retract perforating/guiding rod 140, quadrilateral pawl and actuating rod 130, as well as blade 141 distally into elongated proximal end 222 of telescopic concentric cannula 220.

Following the retraction of blade 141 into elongated proximal end 222 of telescopic concentric cannula 220, detent(s) 102A, 102B can be disengaged from lip 203 (or, in another embodiment groove configured to receive and engage detents 102A, 102B, not shown). Once detent(s) 102A, 102B disposed on the outer surface of proximal portion 111 of the handle member 100, having proximal end 112 are disengaged, biaser 205 will bias flanged distal end 221 of telescopic concentric cannula 220 distally, causing elongated proximal end 222 of telescopic concentric cannula 220 to slidably translate distally, causing expandable anchor sleeve 300 to expand and engage bore 705 in the body cavity wall and adjust the distance between expanded anchor sleeve 300 and the bottom surface of flanged distal end 201 of the flanged sleeve member 200. Handle member 100, as well as perforating/guiding rod 140 and blade 141 are then removed.

Figure 3A:
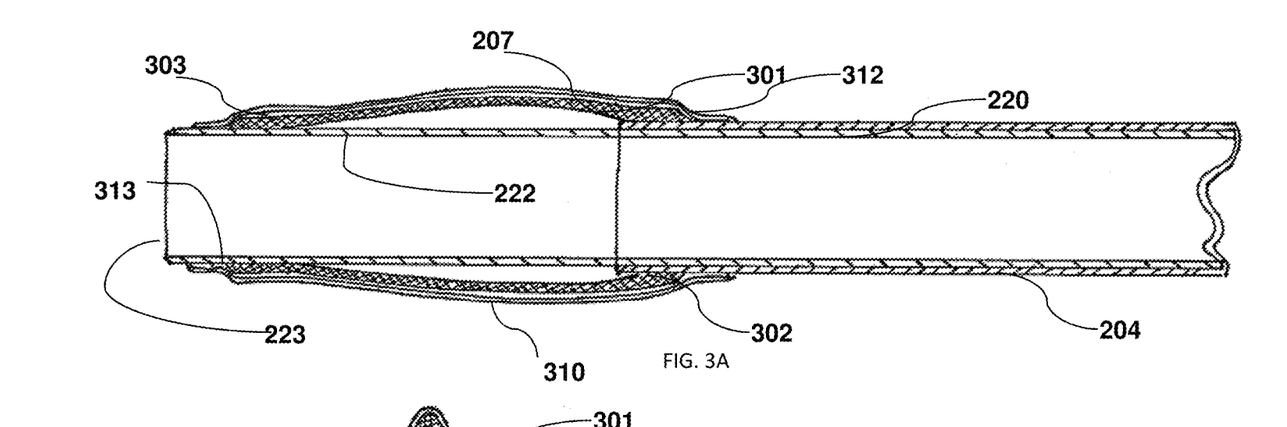
FIG. 3A, illustrates Y-Z cross section of enlarged section A in FIG. 1 of the expanding anchor during actuated insertion, with FIG. 3B illustrating Y-Z cross section of enlarged section A in FIG. 1 of the expanding anchor after expansion of the anchor, upon entering a body cavity.
Figure 3B:
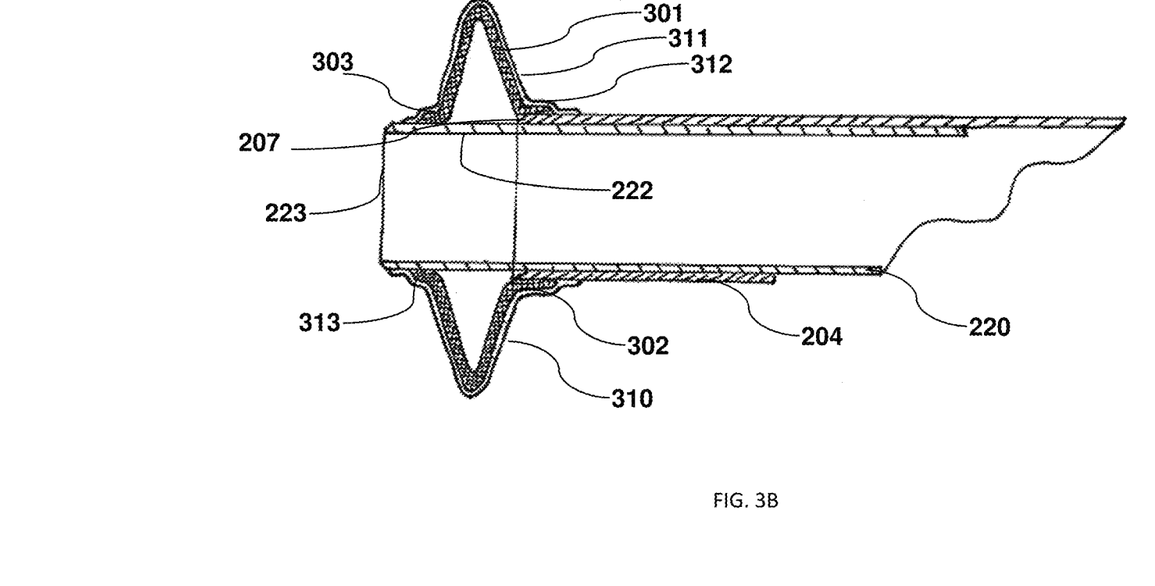

Turning now to FIGS. 3A, 3B, illustrating expanding anchor sleeve 300 in insertion/retraction mode in FIG. 3A, and in expanded, anchoring mode in FIG. 3B. As illustrated in FIG. 3A, when inserted into distally open cylindrical bore 216 (see e.g., FIG. 1), proximal portion's 111 proximal end 112 abuts flanged distal end 221 of telescopic concentric cannula 220 (see e.g., FIG. 1), extending elongated proximal end 222 of telescopic concentric cannula 220 proximally beyond elongated midportion 204 of sleeve member 200, thereby extending expandable anchor 300 having a proximal end 303 operably coupled to elongated proximal end 222 of telescopic concentric cannula 220; and distal end 302 operably coupled to proximal end 207 of sleeve member 200 with a free median portion 301; against adjusting biaser 205 and forming a tube with a substantially uniform outer diameter, the tube being comprised of elongated annular midportion 204 having proximal end 207 of sleeve member 200, expandable anchor sleeve 300 and elongated proximal end 222 of telescopic concentric cannula 220. As further illustrated in FIG. 3A, the expandable anchor, can further comprise flexible curtain 310 similarly having distal end 313 operably coupled to elongated proximal end 222 of telescopic concentric cannula 220; and distal end 312 operably coupled to elongated midportion 204 of sleeve member 200 with a free median portion 311. Upon removal of handle member 100 as described above and as shown in FIG. 3B, biaser 205 (see e.g., FIG. 1) will bias flanged distal end 221 of telescopic concentric cannula 220 distally (see e.g., FIG. 1), causing elongated proximal end 222 of telescopic concentric cannula 220 to slidably translate distally, causing median portion 301 of expandable anchor sleeve 300 and median portion 311 of curtain 310 to expand outwardly from elongated proximal end 222 of telescopic concentric cannula 220 and engage and/or seal bore 705 in the body cavity wall and adjust the distance between expanded anchor sleeve 300 and curtain 310 and the bottom surface of flanged distal end 201 of the flanged sleeve member 200.

Figure 4A:
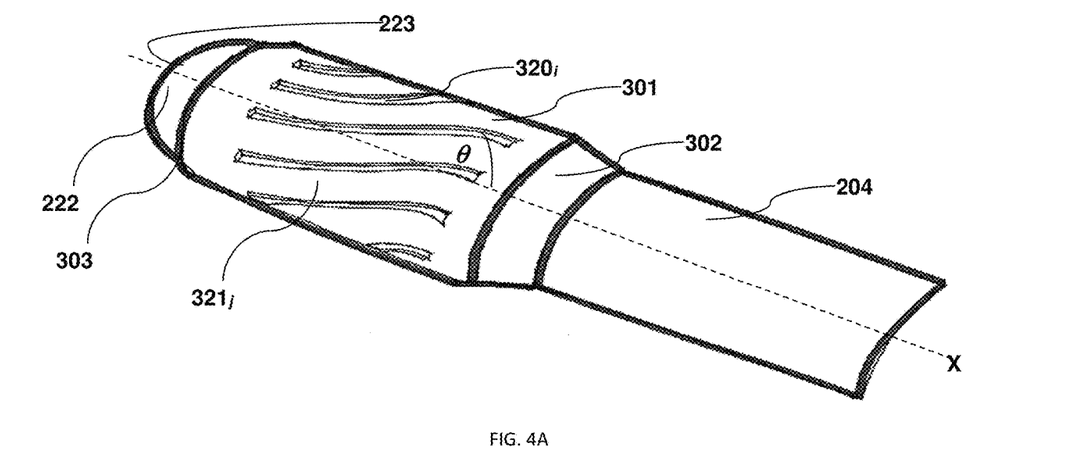
FIG. 4A, illustrates an isometric view of enlarged section A in FIG. 1 of the expanding anchor during actuated insertion, with FIG. 4B illustrating an isometric view thereof after expansion of the anchor, upon entering a body cavity.
Figure 4B:
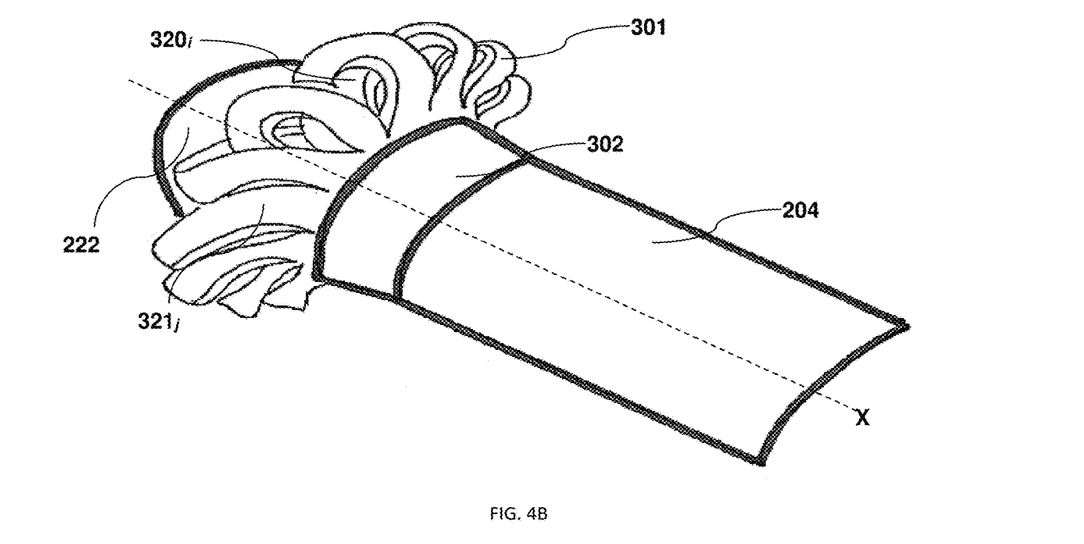

Turning now to FIGS. 4A, 4B, illustrating expanding anchor sleeve 300 in insertion/retraction mode in FIG. 4A, and in expanded, anchoring mode in FIG. 4B. As illustrated in FIG. 4A, expandable anchor sleeve 300 can be comprised of a resilient cylinder having distal end 302 and proximal end 303, with a median portion 301 (wall) defining a plurality of axial slots 320 and wherein slots $320_i$ can be slanted at angle θ of between 1° and about 15° off the longitudinal axis x of handle member 100, and/or elongated proximal end 222 of telescopic flanged concentric cannula 220, slots $320_i$ forming strips $321_j$ therebetween. As illustrated in FIG. 4B, upon removal of handle member 100 as described above and as shown in FIG. 4B, biaser 205 (see e.g., FIG. 1) will bias flanged distal end 221 of telescopic concentric cannula 220 distally (see e.g., FIG. 1), causing elongated proximal end 222 of telescopic concentric cannula 220 to slidably translate distally, causing median portion 301 formed of strips $321_j$ of expandable anchor sleeve 300 to expand outwardly from elongated proximal end 222 of telescopic concentric cannula 220, creating partial overlap of adjacent $j^{th}$ strips $321_j$, thereby imparting rigidity to expandable anchor sleeve 300, that is greater than the rigidity of a sleeve without slanted slots $320_i$. Therefore, in an embodiment, expandable curtain 310 is disposed above median portion 301 (wall) defining plurality of slanted axial slots $320_i$ such that upon expansion, the partial overlap of adjacent $j^{th}$ strips $321_j$, can impart rigidity to expandable anchor sleeve 300, while expandable curtain 310 imparts sealing characteristic to the expandable anchor forming the proximal portion of the adjustable shunt bobbin 20.

Figure 5:
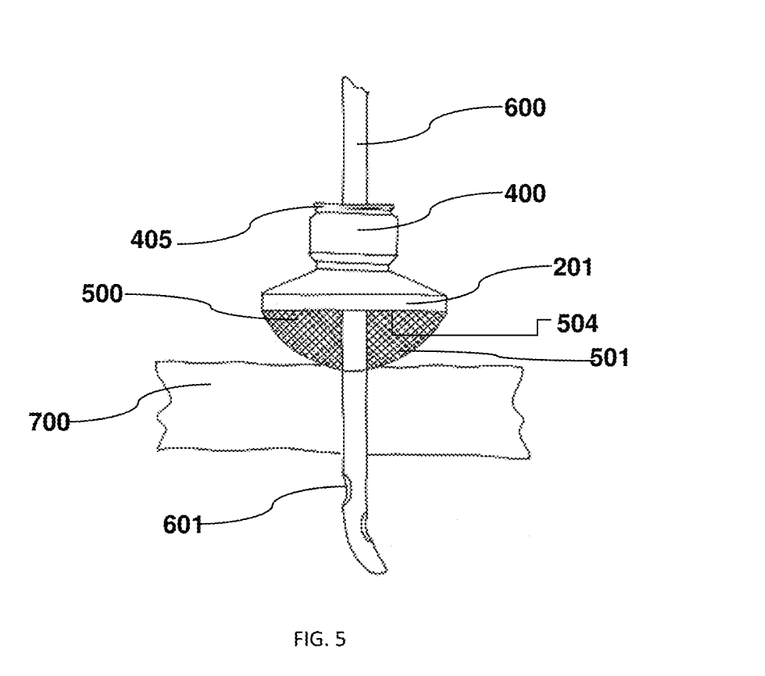
FIGS. 5-9, illustrates a curved cross section sponge in FIG. 5, angled sponge in FIG. 6, split sponge embodiment at normal positioning relative to the body in FIG. 7, tilted right in FIG. 8, and tilted left in FIG. 9.
Figure 6:
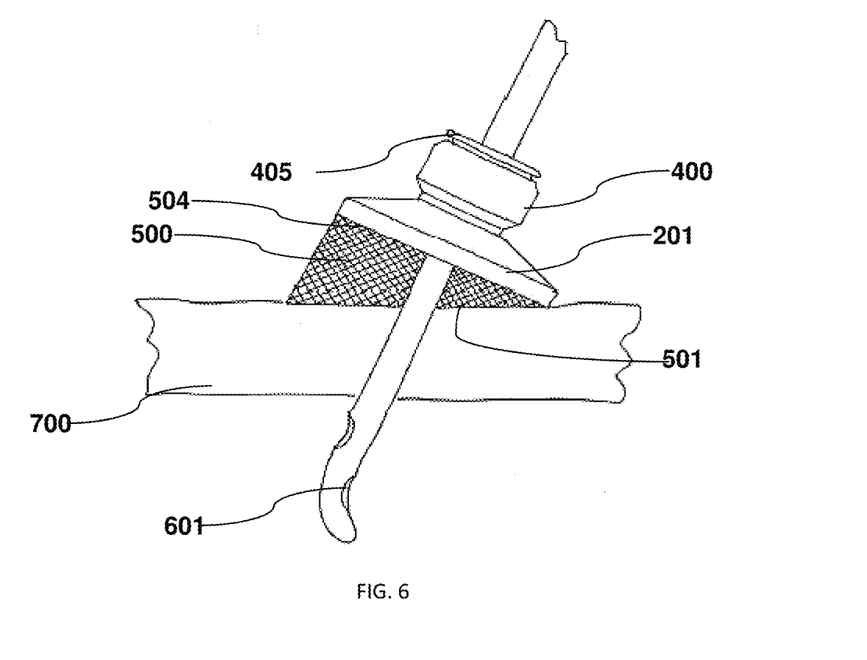

Turning now to FIGS. 5-6, illustrating sponge 500 having bottom surface 501 and an upper surface 504 operably coupled to a bottom surface of flanged distal end 201 of flanged sleeve member 200, sponge 500 configured to be sandwiched between the bottom surface of flanged distal end 201 of flanged sleeve member 200, and the body surface 700. Also shown in FIG. 5, is catheter 600 having at least one distal collection aperture 601 engaged in diaphragm valve having annular body 400, and flexible closure sleeve 405. As illustrated in FIGS. 5 and 6, sponge's 500 bottom surface 501 can define a cross section that is arcuate or curved (FIG. 5) or normal (in other words, in 90°) relative to the longitudinal axis x (see e.g., FIG. 1) of the port. Having an arcuate or curved can enable angular insertion of the port, aiming the collection tube or catheter towards the region required for drainage, for example towards the peritoneum or heart without losing the hermetic seal created in the adjustable shunt bobbin 20. As illustrated in FIG. 6, sponge 500 can have bottom surface 501 that is slanted, such that when abutting the body site 700 bottom surface 501 can form a predetermined angle. The angle can be indication-specific; for example, angling the catheter for hemothorax towards the ribs while angle of approach for other indications may be different. Sponge 500 can be made impregnated with a composition comprising an analgesic, an antiseptic, a disinfectant, a medication, an adhesive (e.g., pressure-sensitive adhesive) or a composition comprising one or more of the forgoing. The angle formed between the longitudinal axis of the port and the body surface can be between about 30° and about 90°, for example, 45°. The foam can be, for example an open-cell poly(urethane) foam, or for example, be made from cellulose, carboxylated butadiene-styrene rubber, polyester foams, hydrophilic epoxy foams or polyacrylate.

Figure 7:
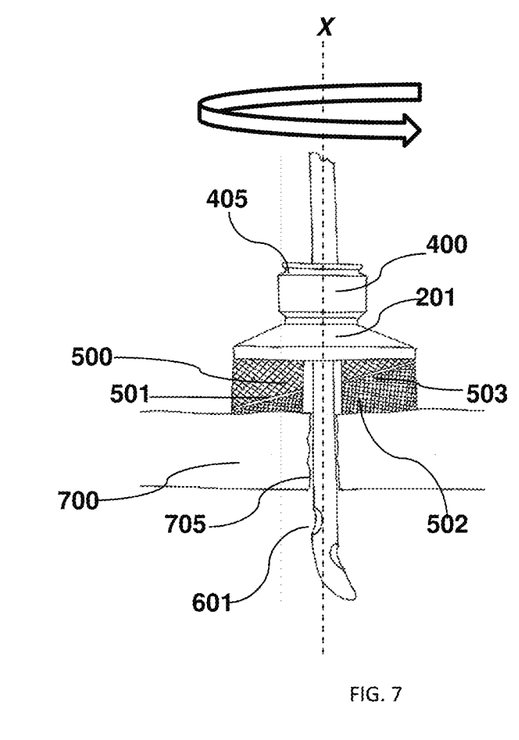
Figures 8, 9:
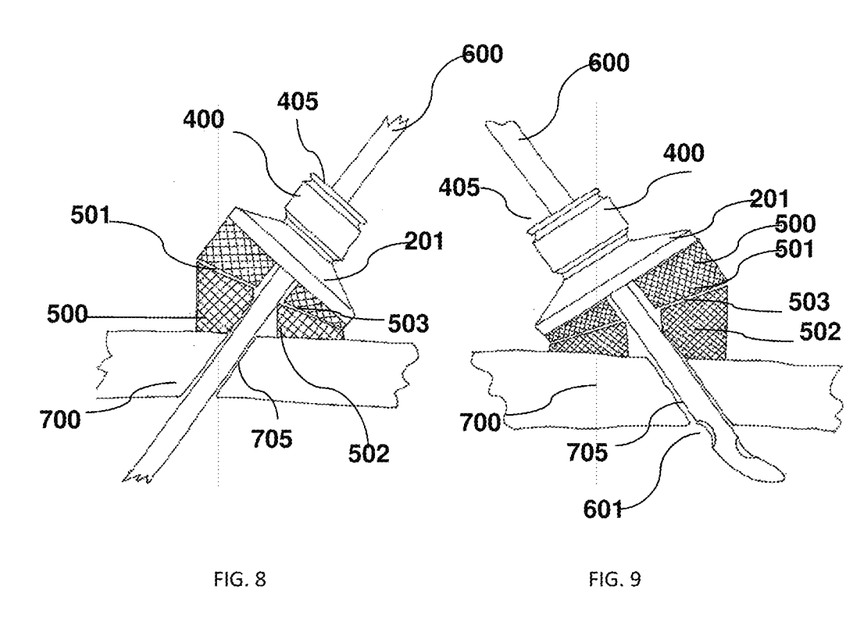

Turning now to FIGS. 7-9, illustrating an embodiment wherein the sponge having the normal bottom surface relative to the port's longitudinal axis is comprised of a first and a second sponge members 500, 502, being rotatably movable relative to each other, first sponge member 500 abutting second sponge member 502 along a complimentary surface 501, 503 defining a slanted cross section relative to longitudinal axis x (see e.g., FIG. 1), of port 10. As illustrated the port can be inserted at a normal (FIG. 7), while for example, clock-wise rotation will tilt the port in one direction (see e.g., FIG. 8) and counter clock wise can tilt the port in another direction (see e.g., FIG. 9). The term "rotatably coupled" is used in its broadest sense to refer to elements which are coupled in a way that permits one element to rotate or pivot with respect to another element.

Accordingly and in an embodiment, provided herein is a kit comprising port 10 as described herein; a catheter; optionally an analgesic; and optionally a disinfectant.

In yet another embodiment, provided herein is diaphragm closure comprising a first annular member, having an internal surface, a external surface, a distal end and a proximal end, the distal end of the external surface defining a radial channel, wherein the internal surface is adapted to operably couple to a predetermined liquid vessel; a second annular member having an internal surface, an external surface, a distal end and a proximal end, the distal end of the internal surface defining a radial channel, wherein the internal surface is operably coupled to the external surface of the first annular member; a flexible closure sleeve having a distal and a proximal annular mounting flanges at opposite ends thereof, with a median mounting flange disposed therebetween, the distal and proximal mounting flanges being engaged respectively in the distally disposed radial channel in the internal surface of the second annular member, and the median mounting flange operably coupled to the radial recess in the external surface of the first annular member, so as to be angularly moveable relative to the first annular member. The predetermined liquid vessel used in conjunction with the diaphragm closure described, can be liquid vessel having a cylindrical distal opening having an interrupted threading thereon (e.g., seltzer bottle), and wherein the internal surface of the first annular member defines a complementary threading therein.

Therefore, provided herein is a pressure sensitive, self-adjustable port, comprising: a handle member comprising pressure sensitive actuation means; a shunt bobbin operably coupled to the handle member, the shunt bobbin comprising: a flanged sleeve member having an elongated annular proximal end and a distal end having a flanged portion and a neck portion; and a telescopic concentric cannula having a flanged distal end and an elongated proximal end, operably slidably coupled to the distal flanged member, the concentric flanged cannula being distally biased; an expanding anchor operably coupled to the elongated proximal end of the telescopic concentric cannula and the elongated annular proximal end of the flanged member; and a perforating blade movable between operational expanded position and retracted stowed position, the perforating blade being operably coupled to the pressure sensitive actuation means, wherein the expanding anchor is biased towards the flanged portion and wherein once actuated, the perforating blade is configured to retract upon entering a body cavity, wherein (i) the handle member comprising a distal head portion defining an internal chamber having a distal end and a proximal end, each distal and proximal end defining a bore therein, the bores being concentrically aligned with a longitudinal axis of the handle member; and a proximal portion defining a axially aligned bore with a detent disposed on an outer surface of the proximal portion, wherein (ii) an actuation knob is operably coupled to the proximal end of the handle member, the actuation knob having a closed distal end and an open proximal end, the proximal open end configured to at least partially accommodate a portion of the pressure sensitive actuation means, wherein (iii) the internal chamber has a proximal end defining radial recess configured to receive and engage at least a portion of the pressure sensitive actuation means, (iv) the pressure sensitive actuation means comprises: an actuation rod having a distal end configured to at least partially engage the actuation knob, and a distal end hingedly coupled to a hinged quadrilateral pawl; the hinged quadrilateral pawl comprising; a first distal pawl member and a second distal pawl member, each first and second pawl member having a distal end and a proximal end with a protrusion configured to engage the recess defined in the proximal end of the chamber defined in the distal head portion of the handle member, and a distal end hingedly coupled to the actuation rod; a first proximal pawl member and a second proximal pawl member, the first proximal pawl member having a distal end hingedly coupled to the first distal pawl member between the distal end and the proximal end of the first distal pawl member, and a proximal end hingedly coupled to a perforating rod, and the second proximal pawl member having a distal end hingedly coupled to the second distal pawl member between the distal end and the proximal end of the second distal pawl member; a pawl biaser configured to bias the distal end of the first proximal pawl member to the distal end of the second proximal pawl member; and a stopper, disposed below the proximal end of the first and second proximal pawl members and above the proximal end of the internal chamber defined in the head portion of the handle member, configured to prevent the proximal end of the first and second proximal pawl members from entering the bore defined in the proximal end of the internal chamber defined in the head portion of the handle member; an actuation biaser operably coupled to the actuation knob and the actuation rod, the actuation biaser configured to distally bias the actuation rod into the actuation knob and the actuation knob distally from the handle member distal end; and the perforating rod, wherein the perforating rod configured to extend beyond the proximal end of the telescopic concentric cannula, wherein (v) the blade is coupled to the perforating rod, wherein (vi) the flanged distal end of the flanged sleeve member defines a distally open cylindrical bore with a diameter configured to accommodate the flanged distal end of the telescopic concentric cannula, and a floor defining a concentric proximal aperture having a diameter configured to accommodate the elongated proximal end of the telescopic concentric cannula, further comprising (vii) an adjusting biaser, disposed in the cylindrical bore defined in the flanged distal end of the flanged sleeve member between the flanged distal end of the telescopic concentric cannula and the floor of the distally open cylindrical bore, (viii) the neck portion of the distal end of the flanged sleeve member defines an external annular surface and an internal annular surface and is configured to releasably engage the detent disposed on an outer surface of the proximal portion of the handle member (ix) the distally open cylindrical bore defines radially disposed lip, configured to receive and engage the detent disposed on an outer surface of the proximal portion of the handle member, wherein (x) the expandable anchor portion comprises a resilient cylinder having a distal end and a proximal end, with a wall defining a plurality of axial slots and wherein the slots are slanted at an angle of between 1° and about 15° off the longitudinal axis of the handle member, wherein (xi) the port of further comprises a diaphragm valve assembly operably coupled to the external surface of the neck portion of the shunt bobbin's sleeve member, the diaphragm valve configured to rotate between an open position and a closed position, (xii) the diaphragm valve assembly comprises: an annular body member being angularly movable relative to the neck portion of the shunt bobbin's sleeve member with an external surface having a distally disposed radial recess; and a flexible closure sleeve having a distal and a proximal annular mounting flanges at opposite ends thereof, with a median mounting flange disposed therebetween, the distal and proximal mounting flanges being engaged respectively in the distally disposed radial recess in the external surface of the annular body member, and the median mounting flange operably coupled to the radial recess in the external surface of the neck portion of the shunt bobbin's sleeve member, so as to be angularly moveable relative to the shunt bobbin's sleeve member, also (xiii) further comprising a sponge having a bottom surface and an upper surface operably coupled to a bottom surface of the flanged distal end of the flanged sleeve member, the sponge configured to be sandwiched between the bottom surface of the flanged distal end of the flanged sleeve member, and the body surface, (xiv) the sponge's bottom surface defines a cross section that is curved or normal relative to the longitudinal axis of the port, (xv) the sponge having the normal bottom surface relative to the port's longitudinal axis is comprised of a first and a second sponge members, rotatably movable relative to each other, the first sponge member abutting the second sponge member along a complimentary surface defining a slanted cross section relative to the longitudinal axis of the port.

In another embodiment, provided herein is a method of coupling a surgical port to a subject's site across from a body cavity comprising: in a wound, or a predetermined site, positioning the proximal end of a pressure sensitive, self-adjustable surgical port, comprising a handle member comprising pressure sensitive actuation means; a shunt bobbin operably coupled to the handle member, the shunt bobbin comprising: a flanged sleeve member having an elongated proximal end and a distal end having a flanged portion and a neck portion; and a telescopic concentric cannula having a flanged distal end and an elongated proximal end, operably slidably coupled to the distal flanged member, the concentric flanged cannula being distally biased; an expanding anchor operably coupled to the elongated proximal end of the telescopic concentric cannula and the elongated proximal end of the flanged member; and a perforating blade movable between operational expanded position and stowed retracted position, the perforating blade being operably coupled to the pressure sensitive actuation means, wherein the flanged member is biased towards the anchor and wherein once actuated, the perforating blade is configured to retract upon entering a body cavity; actuating the pressure sensitive actuation means thereby extending the perforating end; by applying force on the distal end of the handle, perforating the site; and removing the handle member, wherein (xvi) the handle member comprises a distal head portion defining an internal chamber having a distal end and a proximal end, each distal and proximal end defining a bore therein, the bores being concentrically aligned with a longitudinal axis of the handle member; and a proximal portion defining a axially aligned bore with a detent disposed on an outer surface of the proximal portion, and wherein the proximal end defining a pair of radially opposed recesses configured to receive and engage at least a portion of the pressure sensitive actuation means, wherein (xvii) wherein an actuation knob is operably coupled to the proximal end of the handle member, the actuation knob having a closed distal end and an open proximal end, the proximal open end configured to at least partially accommodate a portion of the pressure sensitive actuation means, wherein (xviii) the pressure sensitive actuation means comprises: an actuation rod having a distal end configured to at least partially engage the actuation knob, and a distal end hingedly coupled to a hinged quadrilateral pawl; the hinged quadrilateral pawl comprising; a first distal pawl member and a second distal pawl member, each first and second pawl member having a distal end and a proximal end with a protrusion configured to engage the recess defined in the proximal end of the chamber defined in the distal head portion of the handle member, and a distal end hingedly coupled to the actuation rod; a first proximal pawl member and a second proximal pawl member, the first proximal pawl member having a distal end hingedly coupled to the first distal pawl member between the distal end and the proximal end of the first distal pawl member, and a proximal end hingedly coupled to a perforating rod, and the second proximal pawl member having a distal end hingedly coupled to the second distal pawl member between the distal end and the proximal end of the second distal pawl member; a pawl biaser configured to bias the distal end of the first proximal pawl member to the distal end of the second proximal pawl member; and a stopper, disposed below the proximal end of the first and second proximal pawl members and above the proximal end of the internal chamber defined in the head portion of the handle member, configured to prevent the proximal end of the first and second proximal pawl members from entering the bore defined in the proximal end of the internal chamber defined in the head portion of the handle member; an actuation biaser operably coupled to the actuation knob and the actuation rod, the actuation biaser configured to distally bias the actuation rod into the actuation knob and the actuation knob distally from the handle member distal end; and the perforating rod, wherein the perforating rod configured to extend beyond the proximal end of the telescopic concentric cannula, wherein (xix) actuating the pressure sensitive actuation means, comprises applying force to the actuation knob, (xx) the step of removing the handle member is preceded by removing the force applied to the actuation knob, wherein (xxi) the port further comprises a diaphragm valve assembly operably coupled to the external surface of the neck portion of the shunt bobbin's sleeve member, the diaphragm valve configured to rotate between an open position and a closed position, wherein (xxi) the diaphragm valve assembly comprises: an annular body member being angularly movable relative to the neck portion of the shunt bobbin's sleeve member with an external surface having a distally disposed radial recess; and a flexible closure sleeve having a distal and a proximal annular mounting flanges at opposite ends thereof, with a median mounting flange disposed therebetween, the distal and proximal mounting flanges being engaged respectively in the distally disposed radial recess in the external surface of the annular body member, and the median mounting flange operably coupled to the radial recess in the external surface of the neck portion of the shunt bobbin's sleeve member, so as to be angularly moveable relative to the shunt bobbin's sleeve member, and wherein (xxii) following the step of removing the handle: opening the diaphragm valve; inserting a catheter, cannula, tube, drainage tube or a combination comprising one or more of the forgoing into the body cavity; and closing the diaphragm valve.

In yet another embodiment, provided herein is a kit comprising: the pressure sensitive, self-adjusting surgical port described herein, a catheter; optionally an analgesic; and optionally a disinfectant.

In another embodiment, provided herein is a diaphragm closure comprising a first annular member, having an internal surface, an external surface, a distal end and a proximal end, the distal end of the external surface defining a radial channel, wherein the internal surface is adapted to operably couple to a predetermined liquid vessel; a second annular member having an internal surface, an external surface, a distal end and a proximal end, the distal end of the internal surface defining a radial channel, wherein the internal surface is operably coupled to the external surface of the first annular member; a flexible closure sleeve having a distal and a proximal annular mounting flanges at opposite ends thereof, with a median mounting flange disposed therebetween, the distal and proximal mounting flanges being engaged respectively in the distally disposed radial channel in the internal surface of the second annular member, and the median mounting flange operably coupled to the radial recess in the external surface of the first annular member, so as to be angularly moveable relative to the first annular member, wherein (xxiii) the predetermined liquid vessel is a liquid vessel having a cylindrical distal opening having an interrupted threading thereon, and wherein the internal surface of the first annular member defines a complementary threading therein.

While in the foregoing specification the self-adjusting, perforating and or guiding port configured to automatically retract a perforating blade or guiding cannula upon entering a body cavity described herein have been described in relation to certain embodiments, and many details are set forth for purpose of illustration, it will be apparent to those skilled in the art that the disclosure of the membrane filtration cartridges described herein are susceptible to additional embodiments and that certain of the details described in this specification and as are more fully delineated in the following claims can be varied considerably without departing from the basic principles of this invention.

What is claimed:

1. A pressure sensitive, self-adjustable port, comprising:
  a. a handle member comprising pressure sensitive actuation means;
  b. a shunt bobbin operably coupled to the handle member, the shunt bobbin comprising: a flanged sleeve member having an elongated annular proximal end and a distal end having a flanged portion and a neck portion; and a telescopic concentric cannula having a flanged distal end and an elongated proximal end, operably slidably coupled to the distal flanged member, the concentric flanged cannula being distally biased;
  c. an expanding anchor operably coupled to the elongated proximal end of the telescopic concentric cannula and the elongated annular proximal end of the flanged member; and
  d. a perforating blade movable between operational expanded position and retracted stowed position, the perforating blade being operably coupled to the pressure sensitive actuation means, wherein the expanding anchor is biased towards the flanged portion and wherein once actuated, the perforating blade is configured to retract upon entering a body cavity.

2. The port of claim 1, wherein the handle member comprising a distal head portion defining an internal chamber having a distal end and a proximal end, each distal and proximal end defining a bore therein, the bores being concentrically aligned with a longitudinal axis of the handle member; and a proximal portion defining a axially aligned bore with a detent disposed on an outer surface of the proximal portion.

3. The port of claim 2, wherein an actuation knob is operably coupled to the proximal end of the handle member, the actuation knob having a closed distal end and an open proximal end, the proximal open end configured to at least partially accommodate a portion of the pressure sensitive actuation means.

4. The port of claim 2, wherein the internal chamber has a proximal end defining radial recess configured to receive and engage at least a portion of the pressure sensitive actuation means.

5. The port of claim 4, wherein the pressure sensitive actuation means comprises:
  a. an actuation rod having a distal end configured to at least partially engage the actuation knob, and a distal end hingedly coupled to a hinged quadrilateral pawl;
  b. the hinged quadrilateral pawl comprising;
    i. a first distal pawl member and a second distal pawl member, each first and second pawl member having a distal end and a proximal end with a protrusion configured to engage the recess defined in the proximal end of the chamber defined in the distal head portion of the handle member, and a distal end hingedly coupled to the actuation rod;
    ii. a first proximal pawl member and a second proximal pawl member, the first proximal pawl member having a distal end hingedly coupled to the first distal pawl member between the distal end and the proximal end of the first distal pawl member, and a proximal end hingedly coupled to a perforating rod, and the second proximal pawl member having a distal end hingedly coupled to the second distal pawl member between the distal end and the proximal end of the second distal pawl member;
    iii. a pawl biaser configured to bias the distal end of the first proximal pawl member to the distal end of the second proximal pawl member; and
    iv. a stopper, disposed below the proximal end of the first and second proximal pawl members and above the proximal end of the internal chamber defined in the head portion of the handle member, configured to prevent the proximal end of the first and second proximal pawl members from entering the bore defined in the proximal end of the internal chamber defined in the head portion of the handle member;

c. an actuation biaser operably coupled to the actuation knob and the actuation rod, the actuation biaser configured to distally bias the actuation rod into the actuation knob and the actuation knob distally from the handle member distal end; and d. the perforating rod, wherein the perforating rod configured to extend beyond the proximal end of the telescopic concentric cannula.

6. The port of claim 5, wherein the blade is coupled to the perforating rod.

7. The port of claim 1, wherein the flanged distal end of the flanged sleeve member defines a distally open cylindrical bore with a diameter configured to accommodate the flanged distal end of the telescopic concentric cannula, and a floor defining a concentric proximal aperture having a diameter configured to accommodate the elongated proximal end of the telescopic concentric cannula.

8. The port of claim 7, further comprising an adjusting biaser, disposed in the cylindrical bore defined in the flanged distal end of the flanged sleeve member between the flanged distal end of the telescopic concentric cannula and the floor of the distally open cylindrical bore.

9. The port of claim 8, wherein the neck portion of the distal end of the flanged sleeve member defines an external annular surface and an internal annular surface and is configured to releasably engage the detent disposed on an outer surface of the proximal portion of the handle member.

10. The port of claim 9, wherein the distally open cylindrical bore defines radially disposed lip, configured to receive and engage the detent disposed on an outer surface of the proximal portion of the handle member.

11. The port of claim 9, further comprising a diaphragm valve assembly operably coupled to the external surface of the neck portion of the shunt bobbin's sleeve member, the diaphragm valve configured to rotate between an open position and a closed position.

12. The port of claim 11, wherein the diaphragm valve assembly comprises:

a. an annular body member being angularly movable relative to the neck portion of the shunt bobbin's sleeve member with an external surface having a distally disposed radial recess; and b. a flexible closure sleeve having a distal and a proximal annular mounting flanges at opposite ends thereof, with a median mounting flange disposed therebetween, the distal and proximal mounting flanges being engaged respectively in the distally disposed radial recess in the external surface of the annular body member, and the median mounting flange operably coupled to the radial recess in the external surface of the neck portion of the shunt bobbin's sleeve member, so as to be angularly moveable relative to the shunt bobbin's sleeve member.

13. The port of claim 12, further comprising a sponge having a bottom surface and an upper surface operably coupled to a bottom surface of the flanged distal end of the flanged sleeve member, the sponge configured to be sandwiched between the bottom surface of the flanged distal end of the flanged sleeve member, and the body surface.

14. The port of claim 13, wherein the sponge's bottom surface defines a cross section that is curved or normal relative to the longitudinal axis of the port.

15. The port of claim 14, wherein the sponge having the normal bottom surface relative to the port's longitudinal axis is comprised of a first and a second sponge members, rotatably movable relative to each other, the first sponge member abutting the second sponge member along a complimentary surface defining a slanted cross section relative to the longitudinal axis of the port.

16. The port of claim 1, wherein the expandable anchor portion comprises a resilient cylinder having a distal end and a proximal end, with a wall defining a plurality of axial slots and wherein the slots are slanted at an angle of between 1° and about 15° off the longitudinal axis of the handle member.

* * * * *